United States Patent
Awang et al.

(10) Patent No.: US 7,125,694 B2
(45) Date of Patent: Oct. 24, 2006

(54) PROCESS FOR PRODUCING WAX ESTER FROM DIHYDROXY FATTY ACID

(75) Inventors: Roila Awang, Kajang (MY); Salmiah Ahmad, Bandar Baru Bangi (MY); Mahiran Basri, Serdang (MY); Abu Bakar Salleh, Serdang (MY)

(73) Assignees: Malaysian Palm Oil Board, Selangor Darul Ehsan (MY); Universiti Putra Malaysia, Selangor Darul Ehsan (MY)

( * ) Notice: Subject to any disclaimer, the term of this patent is extended or adjusted under 35 U.S.C. 154(b) by 0 days.

(21) Appl. No.: 10/974,771

(22) Filed: Oct. 28, 2004

(65) Prior Publication Data

US 2005/0192452 A1  Sep. 1, 2005

(30) Foreign Application Priority Data

Feb. 26, 2004 (MY) .............................. PI 20040680

(51) Int. Cl.
*C12P 7/64* (2006.01)

(52) U.S. Cl. ...................................... 435/134; 554/167

(58) Field of Classification Search ................ 554/167; 435/134

See application file for complete search history.

(56) References Cited

U.S. PATENT DOCUMENTS 5,852,080 A * 12/1998 Philbin et al. ................ 524/51

OTHER PUBLICATIONS

Swern et al., JOACS, vol. 67, pp. 902-903, 1945.*
Awang et al., Biotechnology Letters, vol. 26, pp. 11-14, Jan. 2004.*
WPIDS abstr. of SG 86353, 2002.*

* cited by examiner

*Primary Examiner*—Deborah D. Carr
(74) *Attorney, Agent, or Firm*—Bacon & Thomas, PLLC

(57) ABSTRACT

A process for producing wax ester comprising of esterifying dihydroxy fatty acid preferably dihydroxystearic acid with at least one alcohol in the presence of lipase as a catalyst which is then remove by filtration. The filtered catalyst could be reuse and provides a number of cost advantages. In the preferred embodiment of the present invention, the dihydroxystearic acid is derived from palm based oleic acid and the alcohol contains 8 to 18 carbon atoms per molecules.

8 Claims, No Drawings

PROCESS FOR PRODUCING WAX ESTER FROM DIHYDROXY FATTY ACID

FIELD OF INVENTION

The present invention relates to a wax ester, particularly to a palm-based wax ester and the method for producing thereof.

BACKGROUND OF THE INVENTION

Wax esters functionalized with hydroxyl groups in the alkyl chain of fatty acid are of considerable industrial interest compared with the ordinary wax esters because of their different behaviour including solubility, surface properties and thermal stability. It was reported that these types of waxes have a variety of uses such as plasticizers, mold release agent, emulsifiers and chemical intermediate. Sulphonated wax esters of ricinoleic acid are promising surface active compound.

Currently, the main source of hydroxy fatty acid castor oil and ricinoleic acid (one hydroxylated fatty acid) is the only one used in oleochemical industry to produce various types of waxes. However, the quantities of castor oil (hence ricinoleic acid and its derivatives) available on the market are subjected to considerable fluctuations owing to poor harvests in the main growing areas of Brazil and India. Therefore interest has been focused upon new synthetic methods, which are capable of producing analogue products in large quantities with reasonable cost.

Wax esters are produced by reacting a fatty acid and an alcohol at high temperatures in the presence of catalyst—acidic catalysis or metal catalysis. This high-temperature process can lead to degradation of the esters and undesired side reactions; additionally the resulting energy cost is high. Acidic catalysts are usually time consuming and also give relatively low yields. An acidic catalyst is usually utilized when treating fatty materials containing large amounts of free fatty acids. However, the yields of the fatty esters are usually less than the theoretical amount. Moreover, the high acid contents of the reaction complicate the separation and purification of the fatty esters and the glycerine. Furthermore, the products obtained are often rather poor quality and must undergo various refining steps.

Ghoshray, Bhaftacharyya and Mukesh et al., have produced ricinoleic wax ester from *Rhizomucor meihei* lipase-catalyzed esterification of ricinoleic acid or alcoholysis of castor oil. While Lang et al. synthesized wax esters of (S)-17hydroxystearic acid and (R)-3-hydroxydecanoic acid with various lipases.

SUMMARY OF THE INVENTION

Taking above-mentioned aspects into consideration, bio-technological methods, such as bioconversion, become more advantages. Palm-based oleochemicals can be alternatives feedstock for the production of the hydroxylated wax ester using lipase-catalyzed reaction.

Lipase-catalyzed reactions operate at mild conditions, which prevent degradation of starting materials and reduce side reactions. Application of lipases in various biochemical modifications of fats and oils is well established, and the catalytic activity of lipases towards hydroxy fatty acid is also well study by various workers. Several hydroxy wax esters produced in the present invention are useful as a surfactants or chemicals.

It is an object of the present invention to provide a method for producing a high quality palm-based wax esters.

Another object of the present invention is to produce a high quality wax esters by esterified dihydroxy fatty acid preferably dihydroxystearic acid (DHSA) with at least one alcohol in the presence of lipase.

A further object of the present invention is to carry out the above-mentioned process on large-scale in a simple manner.

The present invention is relates to a process for producing a wax ester particularly a palm-based wax ester by esterifiying dihydroxy fatty acid preferably dihydroxystearic acid (DHSA) with at least one alcohol which contains 8 to 18 carbons per molecule.

In the preferred embodiment of the present invention, the DHSA is derived from palm based oleic acid which prepared according to Singapore patent 86353. In another embodiment of the present invention the DHSA may be derived from any other oleic acid. The alcohol used in the present invention can be linear or branched alcohol contains 8 to 18 carbons per molecule.

According to Singapore Patent 86353, a process for preparing dihydroxy fatty acid compound from oleic acid comprising the steps of: a). preparation of peroxyacetic acid by reacting glacial acetic acid with hydrogen peroxide (normally 30% to 50%) in the presence of a suitable catalyst; b). epoxidation of oleic acid with peroxyacetic acid obtained from step (a) at sufficient temperature, with the mole ratio of peroxyacetic acid to oleic acid in the range of 0.5:1.0 to about 1.5:1.0 to form an epoxide; and c). hydrolysis of the epoxide obtained from step (b) to dihydroxy fatty acid compound. Preferably, said dihydroxy fatty acid compound in the present invention is dihydroxystearic acid.

Wax ester is accomplished in accordance with the present invention that the mixture of dihydroxy fatty acid and alcohol is rotating or stirring continuously at temperature in the range from about 30° C. to 70° C. The esterification reaction may be carried out with organic solvent as a medium or without organic solvent at elevated temperature. Preferably lipase is added as a catalyst into the reaction mixture to facilitate the esterification reaction.

DETAILED DESCRIPTION OF THE PREFERRED EMBODIMENTS

According to the present invention, process for producing wax ester comprises esterifying dihydroxy fatty acid compound preferably dihydroxystearic acid (DHSA) with at least one alcohol in the presence of lipase as a catalyst and an organic solvent medium optionally. In the preferred embodiment of the present invention, said DHSA is derived from palm-based oleic acid whereas said alcohol is an alcohol with 8 to 18 carbon atoms per molecule.

Continuously stirring or rotating is applied to the reaction mixture and the mixture is allowed to proceed for about 1 hour. After this, the reaction mixture is separated from the catalyst by filtration. The separated catalyst is then recycled and washed with organic solvent.

In the preferred embodiment of the present invention, the immobilized enzyme is used. There are two main benefits of using immobilized enzyme in this invention. Firstly, immobilized enzyme is an easy separation of the enzyme from the product; and secondly, recycle of the enzyme is allowed. Easy separation of the enzyme from the product simplifies enzyme applications permitting reliable and efficient reaction technology. While enzyme reuse provides a number of cost advantages, which are often prerequisite for establishing an economically viable enzyme-catalyzed process. Lipase used in the present invention is preferably Lipozyme.

The DHSA used in the present invention is 9,10-dihydroxystearic acid which represented by formula (1)

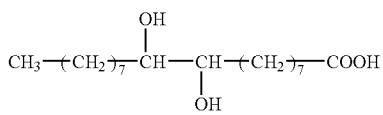

Formula 1

According to Singapore Patent 86353, a process for preparing dihydroxy fatty acid compound from oleic acid comprising the steps of: a). preparation of peroxyacetic acid by reacting glacial acetic acid with hydrogen peroxide (normally 30% to 50%) in the presence of a suitable catalyst; b). epoxidation of oleic acid with peroxyacetic acid obtained from step (a) at sufficient temperature, with the mole ratio of peroxyacetic acid to oleic acid in the range of 0.5:1.0 to about 1.5:1.0 to form an epoxide; and c). hydrolysis of the epoxide obtained from step (b) to dihydroxy fatty acid compound. In the preferred embodiment of the present invention, the ratio of glacial acetic acid to hydrogen peroxide of step (a) is 2.06:1.0; the mole ratio of peroxyacetic acid to oleic acid of step (b) is in the range of 0.75:1.0 to about 1.0:1.0; and the step (b) is conducted in a temperature in the range of 60° C. to 95° C., more preferably at 75° C. to 80° C. When the addition of peroxyacetic acid to the oleic acid is completed, the reaction mixture of step (b) is stirred for about 30 minutes to 3 hours, more preferably from one hour 30 minutes to two hours. Finally, the reaction mixture is separated from unreacted peroxyacetic acid prior to hydrolysis of the epoxide.

In the preferred embodiment of the present invention, the dihydroxy fatty acid compound used is dihydroxystearic acid which derived from palm oil oleic acid.

The ratio of DHSA to alcohol at the beginning of the reaction may be varied in a wide range. In the preferred embodiment of the present invention, to prepare a product which is rich in wax ester and contains only small residual amounts of DHSA and alcohol, DHSA and alcohol will be supplied at a mole ratio in the range of 1:1 to 1:2 with preferably 1:1. If it is desired to minimize the acid content of the wax ester product, it will be recommendable to begin with an excess of alcohol. In this way it is readily possible to prepare wax esters having an acid value below 5. The acid value is measured in the usual manner in mgKOH required per gram of the sample, and is a measure of residual acid.

The fatty acid compositions (FAC) of DHSA and product obtained can be determined by gas chromatography. Other chemical characteristic used to identify DHSA and the products are saponification value (AOCS Method) and acid value (AOCS Method). Table 1 shows the characteristics of palm-based DHSA used in this invention. However, it may be varied depending on the sources of the oleic acid used for the production of DHSA. The process is applicable to crude and purified DHSA.

TABLE 1A

Characteristic of Purified Palm-Based DHSA

| Parameter | | |
|---|---|---|
| Hydroxyl value, mgKOH/g | | 309.3 |
| Acid Value, mgKOH/g | | 180.3 |

TABLE 1A-continued

Characteristic of Purified Palm-Based DHSA

| Parameter | | |
|---|---|---|
| Iodine Value, gI$_2$/100 g | | 1.1 |
| Saponification Value, mgKOH/g | | 178.5 |
| Melting Point, ° C. | | 90.6 |
| Fatty Acid Composition, % | C16:0 | 2.8 |
| | C18:0 | 1.8 |
| | C18:2OH | 93.2 |
| | unknown | 2.2 |

TABLE 1B

Characteristic of Crude Palm-Based DHSA

| Parameter | | |
|---|---|---|
| Hydroxyl value, mgKOH/g | | 196.0 |
| Acid Value, mgKOH/g | | 179.3 |
| Iodine Value, g I$_2$/100 g | | 10.2 |
| Saponification Value, mgKOH/g | | 178.0 |
| Melting Point, ° C. | | 61.9 |
| Fatty Acid Composition, % | C18:2OH | 67.2 |
| | C12-CI8 | 14.2 |
| | unknown | 18.6 |

Table 2 demonstrates the reusability of the immobilized enzyme (in particular Lipozyme IM) used in this invention. The enzyme activity after repeated use was assessed in term of % conversion of DHSA ester at the end of each cycle.

TABLE 2

Reusability of Lipozyme on the esterification of DHSA and 1-Octanol

| Cycle | % Conversion of ester |
|---|---|
| C1 | 92.4 |
| C2 | 91.8 |
| C3 | 92.2 |
| C4 | 91.8 |
| C5 | 90.7 |
| C6 | 91.1 |
| C7 | 89.6 |
| C8 | 88.9 |
| C9 | 89.0 |
| C10 | 87.4 |
| C11 | 87.4 |
| C12 | 82.0 |
| C13 | 82.9 |
| C14 | 79.6 |
| C15 | 70.5 |
| C16 | 79.8 |
| C17 | 78.4 |
| C18 | 81.7 |
| C19 | 81.3 |
| C20 | 85.7 |
| C21 | 70.7 |
| C22 | 67.6 |
| C23 | 65.2 |
| C24 | 64.5 |

The reaction was carried out at 50° C., at rotating speed of 150 rpm for 1 hour, mole ratio of DHSA to 1-octanol=1:2

Wax ester obtainable from the process according to the present invention is 9,10-dihydroxystearate which presented by formula (2):

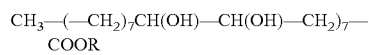

Formula 2 wherein R is independently selected from linear or branched alkyl group with 8 to 18 carbon atoms.

The present invention may be carried into practice in various ways, but certain specific processes embodying the present invention will be described by the way of illustrated in the following examples.

EXAMPLE 1

A batchwise operation was carried out on a laboratory scale. DHSA (0.1 mol) and 1-octanol (0.1 mol) were placed in a 1 L rotary evaporator flask with 10% (w/w). Lipozyme IM based on fatty acid. Hexane was used as a solvent medium. Stirring was achieved by rotating the flask using a rotary evaporator. The reaction was allowed to proceed for 1 h. After this time the reaction mixture was separated from the catalyst. The mixture was then cooled at 5° C. for 5 h. The separated crystals were removed by filtration and washed with hexane.

The product obtained has an acid value of about 40.7 mgKOH/g. The yield is about 63.3% based on GC analysis. FTIR: 1729 $cm^{-1}$ (C=O of ester compound), 1175 $cm^{-1}$ (C—O stretching), 3465 $cm^{-1-3329}$ $cm^{-1}$ (OH stretching)

EXAMPLE 2

Example 1 was repeated. The mixture was heated to 50° C. in a waterbath. The reaction was allowed to proceed for 1 h. The product has an acid value of 16.5 mgKOH/g. The yield was about 76.6% based on GC analysis. FTIR: 1731 $cm^{-1}$ (C=O of ester compound), 1175 $cm^{-1}$ (C—O stretching), 3462 $cm^{-1-3328}$ $cm^{-1}$ (OH stretching)

EXAMPLE 3

Example 1 was repeated. The mixture without organic solvent was heated to 70° C. in a waterbath. The product has an acid value of about 12.9 mgKOH/g. The yield is about 84.1% based on GC analysis. FTIR: 1731 $cm^{-1}$ (C=O of ester compound), 1178 $cm^{-1}$ (C—O stretching), 3467 $cm^{-1-3324}$ $cm^{-1}$ (OH stretching).

EXAMPLE 4

Example 1 was repeated. The mole ratio of DHSA to octanol is 1:2. The reaction mixture was heated to 50° C. in a waterbath. The product has an acid value of 3.9 mgKOH/g. The yield is about 90.1% based on GC analysis. FTI R: 1737 $cm^{-1}$ (C=O of ester compound), 1172 $cm^{-1}$ (C—O stretching), 3464 $cm^{-1-3336}$ $cm^{-1}$ (O—H stretching).

EXAMPLE 5

316.5 g (1 mole) DHSA, 260.4 g (2 mole) 1-octanol and hexane (1500 ml) were added to the multineck reactor, which was fitted with a mechanical stirrer. The reaction mixture was heated to the desired temperature. Then, lipozyme (10% w/w) was introduced into the reactor and stirring begun. The reaction was conducted at 50° C. for 3 h.

The product has an acid value of 3.4 mgKOH/g. The yield is about 92.3% based on GC analysis. FTIR: 1733 $cm^{-1}$ (C=O of ester compound), 1175 $cm^{-1}$ (C—O stretching), 3471 $cm^{-1-3322}$ $cm^{-1}$ (O—H stretching).

EXAMPLE 6

94.95 g (0.3 mole) DHSA, 117 g (0.6 mole) isostearyl alcohol and 450 ml hexane were added to the multineck reactor, which was fitted with a mechanical stirrer. The reaction mixture was heated to 50° C. then Lipozyme was introduced into the reactor and stirring begun. The reaction was conducted for 3 h.

The product has an acid value of 17.8 mgKOH/g. The yield is about 73.3% based on GC analysis. FTIR: 1735 $cm^{-1}$ (C=O of ester compound), 1171 $cm^{-1}$ (C—O stretching), 3467 $cm^{-1-3324}$ $cm^{-1}$ (O—H stretching)

It is to be understood that the present invention may be embodied in other specific forms and is not limited to the sole embodiment described above. However modification and equivalents of the disclosed concepts such as those which readily occur to one skilled in the art are intended to be included within the scope of the claims which are appended thereto.

The invention claimed is:

1. A method for producing wax ester from dihydroxystearic acid, comprising the step of:
    (a) esterifying said dihydroxystearic acid with at least one alcohol in the presence of lipase.

2. A method of claim 1, wherein the lipase is lipozyme.

3. A method of claim 1 wherein said alcohol is linear or branched alcohol with 8 to 18 carbon atoms per molecules.

4. A method of claim 1 wherein the mole ratio of said dihydroxystearic acid to said alcohol is in the range of 1:1 to 1:2.

5. A method of claim 1, wherein said esterification process is conducted at a temperature in the range of 30–70° C.

6. A method of claim 1, wherein said esterification process further includes adding an organic solvent.

7. A method of claim 5, wherein said esterification process is carried out at 50° C. in the presence of said organic solvent.

8. A method of claim 1, wherein the lipase is lipozyme, wherein said alcohol is linear or branched alcohol with 8 to 18 carbon atoms per molecules, wherein the mole ratio of said dihydroxystearic acid to said alcohol is in the range of 1:1 to 1:2, wherein said esterification process is conducted at a temperature in the range of 30–70° C., and wherein said esterification process further includes adding an organic solvent.

* * * * *